United States Patent [19]

Terrill et al.

[11] Patent Number: 4,978,340

[45] Date of Patent: Dec. 18, 1990

[54] SYRINGE WITH RETRACTABLE NEEDLE

[75] Inventors: Richard C. Terrill, Hurst; Fred A. Allgood, Fort Worth; John A. Cunningham, Garland, all of Tex.

[73] Assignee: Alteron Incorporated

[21] Appl. No.: 207,265

[22] Filed: Jun. 15, 1988

[51] Int. Cl.⁵ .............................................. A61M 5/32
[52] U.S. Cl. .................................. 604/195; 604/110; 604/263
[58] Field of Search ............... 604/110, 195, 196, 198, 604/187, 218, 263

[56] References Cited

U.S. PATENT DOCUMENTS

| | | |
|---|---|---|
| 3,937,211 | 2/1976 | Merten . |
| 4,026,287 | 5/1977 | Haller . |
| 4,425,120 | 1/1984 | Sampson et al. ................... 604/198 |
| 4,507,117 | 3/1985 | Vining et al. ........................ 604/196 |
| 4,650,468 | 3/1987 | Jennings, Jr. ....................... 604/110 |
| 4,675,005 | 6/1987 | DeLuccia ............................ 604/110 |
| 4,692,156 | 9/1987 | Haller ................................. 604/110 |
| 4,710,170 | 12/1987 | Haber et al. ........................ 604/110 |
| 4,747,830 | 5/1988 | Gloyer et al. ...................... 604/110 |

Primary Examiner—John D. Yasko
Attorney, Agent, or Firm—Richards, Medlock & Andrews

[57] ABSTRACT

The invention discloses a syringe construction which permits use of standard hypodermic needles and allows the hypodermic needle to be retracted into the body of the syringe after use to minimize accidental pricking from the needle by withdrawing the needle into the syringe body such that it is not exposed. The invention provides for a syringe body having an engaging thread on the distal end for receiving a hypodermic needle, adjacent to the engaging thread is a positioning groove and locking surfaces for engaging a needle carrier, a needle carrier is removably engaged to the body which has a distal end which will mate with the needle and a proximal end providing an engaging means for engaging the syringe plunger. The plunger has a engaging means for engaging the needle carrier such that the needle carrier can be rotated and retracted into the syringe body.

15 Claims, 2 Drawing Sheets

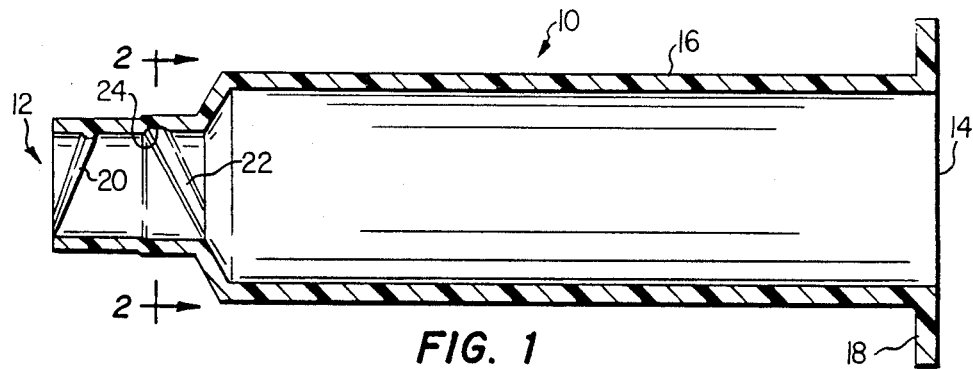
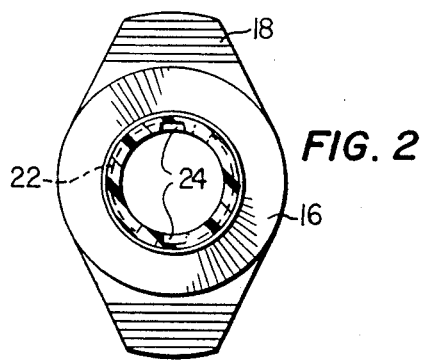
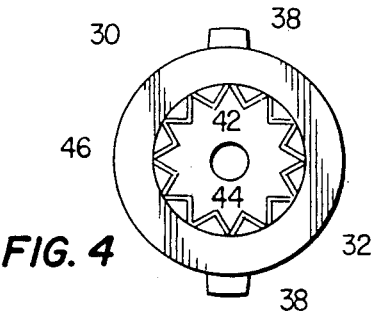
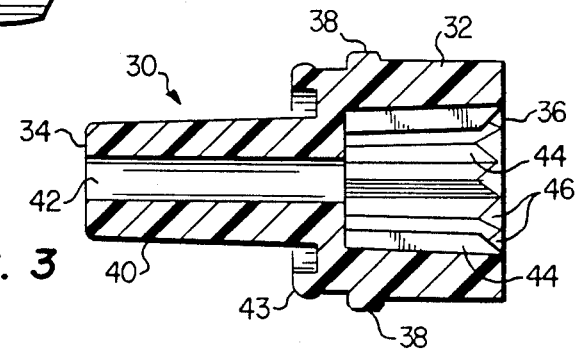
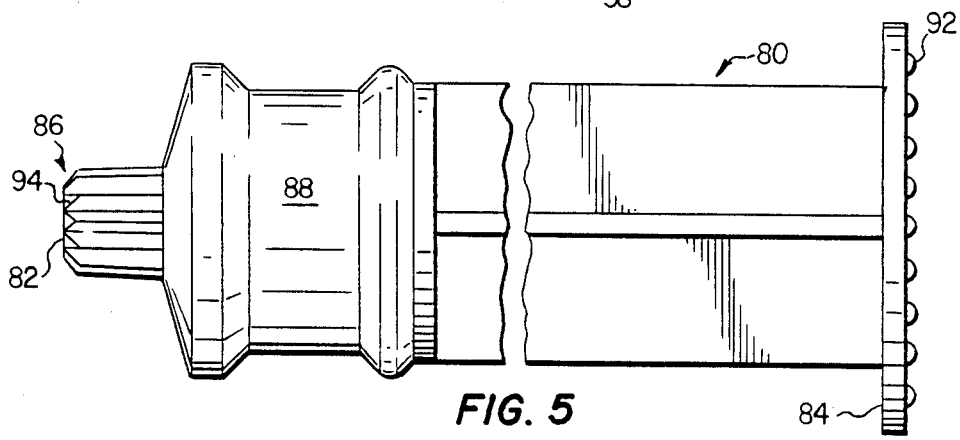

SYRINGE WITH RETRACTABLE NEEDLE

TECHNICAL FIELD

The present invention relates to the medical arts and in particular a hypodermic syringe constructed such that the needle may be retracted into the syringe body after use.

BACKGROUND ART

Hypodermic syringes are utilized in the medical field to inject fluids into the body or to remove fluids from the body. At present, syringe bodies are sold commercially in a number of different sizes. However, common to each size or capacity of syringe body is a distal end which has a standard needle engaging thread-like projection. Similarly, hypodermic needles are manufactured in a variety of diameters and lengths for various purposes. Commercially available needles, however, no matter the length or diameter, all have a standard hub which engages with the standard threads on the various syringe bodies. Through this standardization, different size needles can be utilized with different size syringe bodies, thus avoiding the need for a different set of needles for each size of syringe.

Currently, the prevalent practice in the industry is to attach the needle to the desired syringe body, utilize the needle, then cap the needle and discard the syringe along with the capped needle. Typically, the needle cap is slightly larger in diameter than the needle. The process of capping the needle after use subjects the health care workers to accidental pricking from the needle. This in turn creates a risk of infection from a contaminated needle which is highly undesirable especially for such diseases as AIDS.

Various attempts to protect health care workers from accidental pricking have been proposed. One such method is to provide a slidable sleeve over the syringe body which after use of the syringe can be slid into place over the needle such as shown in U.S. Pat. No. 4,425,120. This device would have the drawback of limiting or distorting visibility and measurement of the syringe contents. Also, the device would not be easily moldable.

Others have suggested the provision of a retractable needle which after use is pulled back into the body of the syringe to thereby eliminate exposure of the sharp needle tip. One such attempt is shown in U.S. Pat. No. 4,026,287 wherein the syringe body is constructed such that the needle is formed into the front of the syringe, and the front of the syringe is connected to the side wall by an area of serration. After use of the syringe, the plunger engages the front portion of the syringe body and force is applied to break the serrations, after which the front of the syringe and needle can be retracted into the syringe body. Such design appears to offer a structure which is likely to break when the needle is in the patient, if the structure is such that it can be easily broken to retract the needle. U.S. Pat. No. 4,507,117 discloses a needle which forms an integral part of a slidable piston which can be moved within the syringe to expose the needle or to retract the needle. This device will not accept standard needles. U.S. Pat. No. 4,675,005 illustrates a needle which is adapted to be threaded into the syringe body and which may be engaged by a plunger in order to retract the needle. A number of variations of design are presented which have undesired dead volume or undesirable connecting apparatus. U.S. Pat. No. 4,650,462 discloses a retractable needle syringe apparatus of rather complex construction. The attempts to provide for a retractable needle have all required special construction of the syringe body and the needle. These patents require special needle constructions and have not been commercially produced. U.S. Pat. No. 4,710,170 discloses a retractable syringe needle apparatus of complex construction which utilizes standard needles. None of the patents are believed to disclose a device which has been commercially accepted.

Thus, there has been a continuing need for a syringe device which provides the ability to retract a needle into the syringe body which can utilize standard needles, is simple in construction, manufacture, and assembly, is simple to use, and which does not provide significant dead volume.

SUMMARY OF THE INVENTION

The present invention provides a syringe adapted to provide a mechanism for retracting a needle into the body of the syringe after use. The apparatus includes a syringe body formed by a wall defining the syringe body and having a passageway throughout. At the distal end of the syringe body is positioned a needle engaging means for attaching a needle to the syringe body and which also serves to mount the needle on the retractable needle carrier. Adjacent to the needle engaging means is a carrier engaging means for engaging a retractable needle carrier and holding the carrier in place until the carrier is retracted. The syringe body has a proximal end open to receive a plunger. In combination with the syringe body is the carrier which is removably attached to the syringe body. The retractable needle carrier comprises a wall which defines a passageway therethrough which has a distal and proximal end. Disposed on the outside of the carrier wall is a syringe body engaging means for engaging the carrier engaging means of the syringe body. The distal end of said carrier is dimensioned such that it can engage the needle and a plunger engaging means is disposed at the proximal end of the carrier for engaging the plunger. A plunger is also provided which has a rigid body of predetermined length. Attached to the distal end is a carrier engaging means for engaging the plunger engaging means of the carrier. Adjacent to the carrier engaging means is a sealing member to provide a liquid tight slidable seal with the syringe body. On the proximal end of the plunger is a surface to provide an area for force to be applied for manipulation of the plunger.

BRIEF DESCRIPTION OF THE DRAWINGS

A better understanding of the invention and its advantages will be apparent from the Detailed Description taken in conjunction with the accompanying Drawings, in which:

FIG. 1 is a cross-sectional view of the syringe body;

FIG. 2 is a cross-sectional area of the syringe body taken across line A—A of FIG. 1;

FIG. 3 is a cross-sectional area of the needle carrier;

FIG. 4 is a cross-sectional view of the needle carrier taken along line B—B of FIG. 3;

FIG. 5 is a side view of a plunger without;

DETAILED DESCRIPTION

Figure 7:
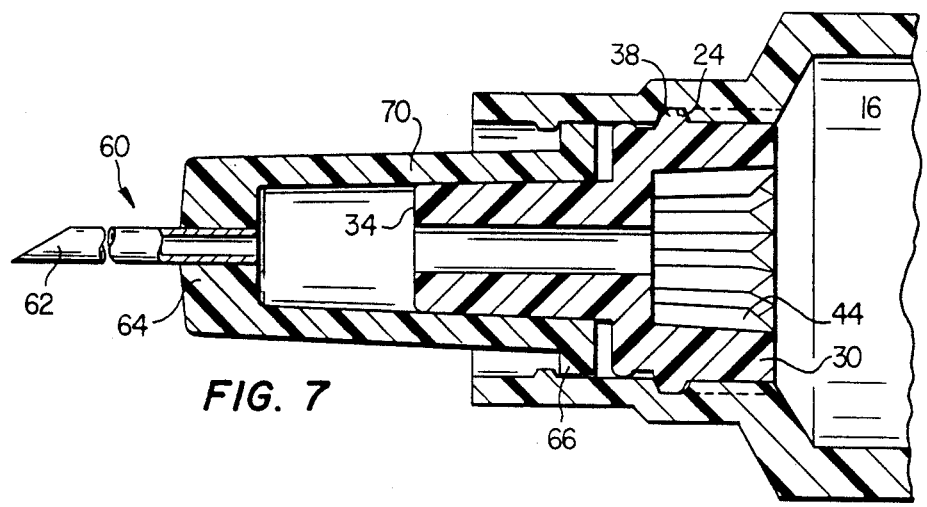
FIG. 7 is a cross-sectional view of the needle carrier in place on the syringe body with the needle in place on the syringe body.

FIG. 1 shows a cross-sectional area of a syringe body 10. The syringe body has a distal (front) end 12 and a proximal (rear) end 14. The body is formed from a syringe wall 16 which defines a passageway therethrough. At the proximal end are finger tabs 18. The distal end 12 is provided with a needle engaging means, which in FIG. 1 is thread surface 20. Preferably, the opening in the distal end and the thread surface 20 are dimensioned such that they will cooperate and engage commercially available standard hypodermic needles. Adjacent to the needle engaging means is the needle carrier engaging means. As illustrated in FIG. 1, the needle carrier engaging means is positioning grooves 22 and locking surface 24, preferably grooves 22 are spiral. (Only one groove shown in cross section). In the preferred embodiment, the spiral provides a rotating motion to engage the needle carrier into the body. It is also preferred that thread surface 20 be oriented such that it rotates the needle in the direction opposite to the direction of rotation imparted to the needle carrier by the positioning grooves 22.

FIG. 2 shows a cross-sectional area of the syringe of FIG. 1 taken across line A—A. Shown is syringe wall 18 and locking surfaces 24. In the preferred embodiment, the locking surface is a flat surface perpendicular to the axis of the syringe body. However, the locking surface may be the end of positioning grooves 22 and does not need to be a flat surface perpendicular to the axis of the syringe body.

FIG. 3 is a cross-sectional view of the needle carrier generally indicated as 30 formed by carrier wall 32 which defines a passageway therethrough and has a distal end 34 and a proximal end 36. The carrier includes syringe body engaging means which cooperate with the carrier engaging means of the syringe body. As illustrated in FIG. 3, these are lugs 38 which extend from the carrier and are dimensioned so as to fit into positioning grooves 22 of the body 10. The outer surface 40 of the distal end 34 is dimensioned such that it will frictionally engage the needle. In a preferred embodiment, it is dimensioned so as to frictionally engage the interior of the hub of standard commercial needles. The passageway 42 is of any desired diameter. The carrier may also have on its outer surface a sealing bead 43 to assure an air-tight liquid-tight seal of the carrier with the syringe body. At the proximal end of the carrier is plunger engaging means for engaging the plunger to provide for retraction of the needle carrier into the body of the syringe. In FIG. 3, the plunger engaging means is illustrated by multiple splines 44 which at their proximal ends have camming surfaces 46. Preferably the retractable needle will be positioned in the syringe body at the time of manufacture.

FIG. 4 is an end view from the proximal end of the carrier 30. Illustrated are lugs 38, wall 32, splines 44, and camming surfaces 46. In a preferred embodiment, a plurality of splines, and preferably more than ten, are provided. Preferably the splines have camming surfaces at the proximal end angled such that no portion of surfaces which initially contacts the carrier engaging means has surfaces perpendicular to the axis of the syringe body are provided around the full circumference of the splines. Camming surfaces having a pitch of about 30° to about 40° have been found suitable. These camming surfaces provide for orientation of the splines of the needle carrier and the plunger such that they mate and slidably engage one another. This plurality of camming surfaces and splines is very useful in providing smooth accurate delivery of medication from the syringe to the patient.

FIG. 7 is a cross-sectional view of the distal end of the syringe body 16 with the carrier 30 in place. As illustrated, engaging lugs 38 have been passed through grooves 22 and mated on locking surface 24. Sealing bead 44 is in contact with the wall 16 of the syringe providing a liquid-tight seal. A standard needle 60 is shown in cross-section comprising a partial view of the hypodermic needle 62 and the needle hub 64. Needle hub 64 has projections 66 which cooperate with engaging thread surface 20 which locks the needle 60 in place such that frictional contact is made between the inner wall of needle hub 64 and the distal end 24 of carrier 30 along the joint at 70.

FIG. 5 is a side view of a plunger assembly useful in the present invention. Plunger body 80 has a distal end 82 and a proximal end 84. Disposed at the distal end is carrier engaging means 86 and adjacent to carrier engaging means is a slidable sealing means such as seal 88. The seal 88 is dimensioned so as to be slidable within the syringe body while providing a liquid seal. The body 90 of the plunger may be of any suitable design which provides sufficient rigidity for manipulation of a plunger. At the distal end 84 the plunger is surface 92 which is useful for manipulation of the plunger by the user or fingers. The seal 88 may be of any suitable material such as that currently used on plungers. The plunger is of sufficient length such that a portion of the plunger will extend beyond the proximal end of the syringe body when the plunger is pushed fully into the syringe body and the needle carrier when the carrier is engaged with the syringe body.

Figure 6:
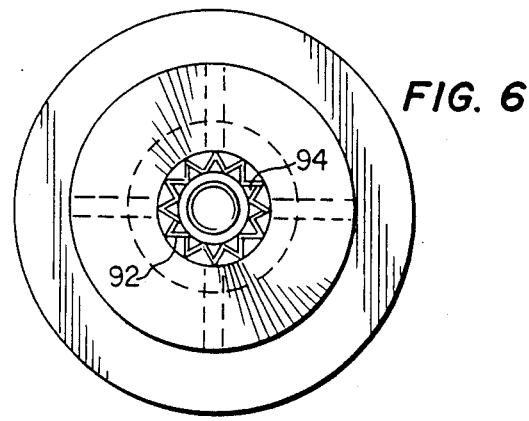
FIG. 6 is an end view of the plunger looking at the engaging end of the plunger.

FIG. 6 is an end view of the plunger from the distal end. The illustrated carrier engaging means are splines 94 which are dimensioned to cooperate and slidably engage with splines 44 of the needle carrier. The splines 44 and 94 provide a mating surface between the two splines such that substantially all of the space is filled by the splines when the two splines of splines are fully engaged to prevent dead volume. Each of the splines on the distal end has a camming surface 96 which interacts with the camming surfaces 46 of splines 44 to provide rotation and alignment of a plunger such that the splines will engage and travel into the female splines of the needle carrier. Preferably a plurality of splines sufficient to correspond with the needle carrier are provided.

Figure 8:
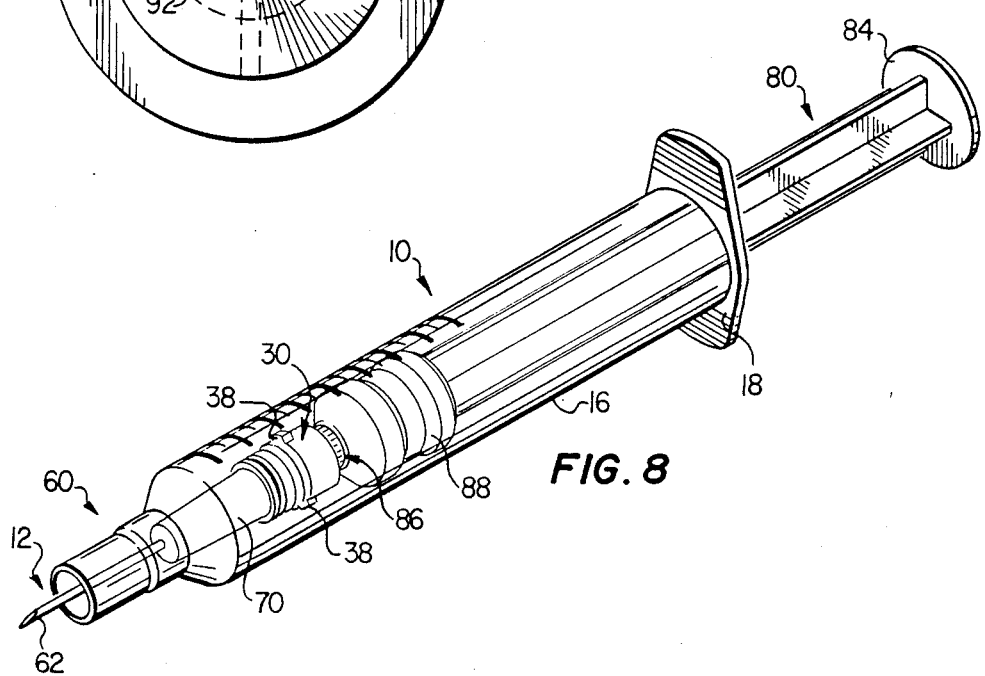
FIG. 8 is a perspective view showing the needle retracted into the syringe body.

FIG. 8 is a perspective view of the syringe body 10 with the plunger 80 retracted carrying the needle 60 and needle carrier 30 into the body of the syringe to thereby allow elimination the pricking hazard of the needle 62.

It is contemplated that the needle carrier will be inserted in the syringe body as it is manufactured for sale. The groove of the body which engages the needle carrier and imparts a rotating action to lock the needle carrier in place should have a direction of rotation opposite the direction of rotation for the needle engaging thread 20. This is desirable because when the needle is mounted on the syringe containing a carrier, the direction for turning a needle to attach the needle onto the syringe will be opposite of that for engaging the needle carrier thereby preventing the needle carrier from being dislodged by the mounting procedure for the needle.

When the direction of rotation is the same for mounting a needle and disengaging the carrier from the syringe body, a possibility is created that during the mounting of the needle, the needle could be partially or completely disengaged from the syringe body prior to when desired. After a suitable needle has been placed on the syringe, it can be utilized in any of the known methods. For example, it can be utilized to withdraw blood or to administer medication. In case of administrating medication, the syringe plunger is pushed forward, the needle is placed in the medication, the plunger is retracted towards the proximal end without rotation, thereby pulling medication into the syringe and leaving the needle carrier engaged with the syringe wall. After the needle has been placed in the patient, the plunger is pushed forward to expel the medication through the needle carrier and then through the needle into the patient. The high number of splines and the camming surfaces are desirable such that when the distal end of the plunger comes into contact with the proximal end of the needle carrier that the alignment and travel of the needle engaging means of the plunger into the plunger engaging means of the carrier is smooth and continuous. Also, it is desired that the spline arrangement or that the engaging arrangement be such that substantially all the space is filled in when the engaging apparatus is fully mated. This is important because it eliminates dead space thereby assuring that accurate dispensing of medication is achieved.

After the fluid is expelled from the syringe the plunger is rotated in a direction to disengage the needle carrier from the engaging means on the syringe body. By this action, lugs 38 of the needle carrier follow the path of grooves 22 as a result of the rotation, thereby traveling towards the proximal end of the syringe. Once the positioning groove is disengaged, the needle carrier can be drawn directly back into the syringe body. The needle rotates and retracts with the needle carrier due to frictional engagement of the needle mount 64 and the distal end 34 of the needle carrier. The needle carrier is retained on the plunger by friction at the small angular fit of the splined parts. This frictional fit is assisted by the forces applied when the carrier is rotated rearward.

The needle can be retracted such that it is completely within the syringe body, thereby minimizing the hazard of accidental pricking.

The present invention as constructed utilizes those materials commonly known and utilized in the manufacture of syringes. The present invention is easily moldable and manufactured.

One skilled in the art will recognize that it is possible to construct this invention from a variety of materials in a wide range of sizes. While the preferred embodiments of the present invention have been described in detail, and shown in the accompanying Drawings, it will be evident that various further modifications are possible without departing from the scope of the invention.

We claim:

1. A syringe apparatus comprising:
   (a) a wall defining a syringe body having a passageway therethrough having a distal end and a proximal end;
   (b) a needle engaging means positioned at the distal end for attaching a needle to the syringe body;
   (c) a carrier engaging means on said syringe body adjacent to said needle engaging means for holding a retractable needle carrier, said needle engaging means and said carrier engaging means rotatably engage the needle and needle carrier in opposite directions of rotation;
   (d) a needle carrier retractably engaging said carrier engaging means comprising:
      (i) a carrier wall defining a passageway therethrough having a distal end and a proximal end;
      (ii) syringe body engaging means on the outer wall of said needle carrier for engaging the carrier engaging means of said syringe body;
      (iii) plunger engaging means located at the proximal end of said needle carrier for engaging a plunger such that the needle carrier means may be retracted into the syringe body upon manipulation of the plunger;
      (iv) needle engaging surface on the distal end of said needle carrier for engaging the needle.

2. The apparatus of claim 1 further comprising:
   (a) a plunger body having a distal end and a proximal end and of sufficient length that a portion of the body will extend beyond the proximal end of said syringe body when said plunger body is pushed completely into the syringe body;
   (b) a carrier engaging means for engaging the carrier engaging means to allow retraction of the needle carrier means into the said syringe body and located at the distal end of the plunger body;
   (c) a sealing means located adjacent to the carrier engaging means for providing a slidable seal with the interior wall of said syringe body; and
   (d) a surface located at the proximal end of said plunger body which permits manipulation of the plunger body.

3. A syringe apparatus comprising:
   (a) a wall defining a syringe body having a passageway therethrough having a distal end and a proximal end;
   (b) a needle engaging means positioned at the distal end of said syringe body for positioning a needle on the syringe body;
   (c) a carrier engaging means on said syringe body for holding a retractable needle carrier;
   (d) a needle carrier means retractably engaging said carrier engaging means comprising:
      (i) a carrier wall defining a passageway therethrough having a distal end and a proximal end;
      (ii) a syringe body engaging means on the outer wall of said needle carrier means for engaging the carrier engaging means of said syringe body;
      (iii) a needle engaging surface on the distal end of said needle carrier;
      (iv) a needle carrier sealing means located adjacent to said syringe body engaging means for assurance of a liquid-tight seal between said needle carrier means and said syringe body when said needle carrier is fully mated with said syringe body;
      (v) the distal end of said needle carrier being dimensioned to frictionally engage a needle;
      (vi) a plunger engaging means formed by a plurality of splines at the proximal end of said needle carrier for engaging a plunger to permit retraction of said needle carrier into said syringe body.
   (e) a plunger comprising:
      (i) a plunger body having a distal end and a proximal end, said plunger body of sufficient length such that a portion of said plunger body will extend beyond the proximal end of said syringe body when said plunger body is pushed completely into said syringe body;
(ii) a needle carrier engaging means formed by a plurality of splines located on the distal end of said plunger body for engaging said needle carrier means to allow for retraction of said needle carrier means into said syringe body;
(iii) a seal which slidably engages the inner wall of said syringe body, said seal located adjacent to said needle carrier engaging means and providing a slidable seal with the interior wall of said syringe body; and
(iv) a proximal end having a surface which permits manipulation of said plunger body.

4. The apparatus of claim 3 wherein said needle engaging means positioned at the distal end of said syringe body for positioning a needle to said syringe body is a thread surface located on the inner wall of said syringe body.

5. The apparatus of claim 3 wherein said carrier engaging means on said syringe body is comprised of positioning grooves located on the interior wall of said syringe body.

6. The apparatus of claim 3 wherein said syringe body engaging means of needle carrier comprises engaging lugs which mate with and rotate relative to said positioning grooves means to provide retractable engagement of said needle carrier means to said syringe body.

7. The apparatus of claim 3 wherein the splines of said plunger engaging means are formed on the proximal end of the interior of said needle carrier wall and said splines of said carrier engaging means of the plunger are formed on the outer portion of the distal end of said plunger body.

8. The apparatus of claim 7 wherein each spline of said plunger engaging means has a camming surface located at the proximal end and having a pitch suitable to provide for orientation of said needle carrier engaging means located on the distal end of said plunger body such that the splines of said plunger body mates with and slidably engages said needle carrier means.

9. The apparatus of claim 3 wherein the needle carrier engaging means further comprises a mating surface means for interaction with said plunger engaging means located on the proximal end of said needle carrier.

10. A syringe apparatus comprising:
(a) a wall defining a syringe body having a passageway therethrough having a distal end and a proximal end;
(b) a thread surface positioned at the distal end for attaching a standard hypodermic needle to the syringe body;
(c) a carrier engaging means on said syringe body adjacent to said thread surface for holding a retractable needle carrier;
(d) a needle carrier retractably engaging said carrier engaging means comprising:
(i) a carrier wall defining a passageway therethrough having a distal end and a proximal end;
(ii) syringe body engaging means on the outer wall of said needle carrier for engaging the carrier engaging means of said syringe body;
(iii) a plunger means to provide slidable frictional engagement located at a proximal end of said needle carrier for engaging a plunger such that the needle carrier means may be retracted into the syringe body upon manipulation of the plunger; and
(iv) the distal end of said needle carrier dimensioned to engage a standard hypodermic needle.

11. The apparatus of claim 10 wherein said carrier engaging means is a positioning groove located on the interior of said wall body.

12. A syringe apparatus comprising:
(a) a wall defining a syringe body having a passageway therethrough having a distal end and a proximal end;
(b) a needle engaging means positioned at the distal end of said syringe body for rotatably positioning a needle on the syringe body;
(c) a carrier engaging means on said syringe body for rotatably holding a retractable needle carrier, said needle engaging means and said carrier engaging means rotatably engage the needle and needle carrier in opposite directions;
(d) a needle carrier means retractably engaging said carrier engaging means comprising:
(i) a carrier wall defining a passageway therethrough having a distal end and a proximal end;
(ii) a syringe body engaging means on the outer wall of said needle carrier means for engaging the carrier engaging means of said syringe body;
(iii) a needle carrier sealing means located adjacent to said syringe body engaging means for assurance of a liquid-tight seal between said needle carrier means and said syringe body when said needle carrier is fully mated with said syringe body;
(iv) the distal end of said needle carrier being dimensioned to functionally engage a needle;
(v) a plunger engaging means at the proximal end of said needle carrier for engaging a plunger to permit retraction of said needle carrier into said syringe body.
(e) a plunger comprising:
(i) a plunger body having a distal end and a proximal end, said plunger body of sufficient length such that a portion of said plunger body will extend beyond the proximal end of said syringe body when said plunger body is pushed completely into said syringe body;
(ii) a needle carrier engaging means located on the distal end of said plunger body for engaging said needle carrier means to allow for retraction of said needle carrier means into said syringe body;
(iii) a seal which slidably engages the inner wall of said syringe body, said seal located adjacent to said needle carrier engaging means and providing a slidable seal with the interior wall of said syringe body; and
(iv) a proximal end having a surface which permits manipulation of said plunger body.

13. The apparatus of claim 12 wherein plunger engaging means located at the proximal end of said needle carrier means for engaging with said plunger body and the needle carrier engaging means of the plunger are a plurality of splines.

14. A syringe apparatus comprising:
(a) a syringe wall defining a syringe body having a passageway therethrough having a distal and proximal
(b) a thread surface positioned on the interior of said syringe wall and positioned at the distal end of said syringe body;

(c) positioning grooves located on the interior of said syringe wall for retractably engaging a needle carrier;

(d) a retractable needle carrier retractably engaged within said syringe body and retractably engaging said positioning grooves, said needle carrier comprising:
  (i) a carrier wall defining a passageway therethrough having a distal end and a proximal end;
  (ii) positioning lugs located on the outer wall of said needle carrier for engaging the positioning grooves of said syringe body;
  (iii) the outer distal surface of said carrier wall dimensioned such that it will frictionally engage a needle;
  (iv) spline surfaces located on the interior of said needle carrier wall at the proximal end of said needle carrier body for slidably engaging mating spline surfaces on a plunger; and (e) a plunger comprising:
  (i) a plunger body having a distal end and a proximal end and of sufficient length such that a portion of said plunger body will extend from the proximal end of said syringe body when said plunger is fully inserted into said syringe body;
  (ii) splines located at the distal end of said syringe body dimensioned to mate with the splines of said needle carrier;
  (iii) a seal located adjacent to said splines of the plunger for providing a slidable seal with the inner surface of said syringe wall; and
  (iv) a surface at the proximal end of said plunger for manipulation of the plunger user.

15. The apparatus of claim 14 wherein said thread surface and said positioning grooves impart rotation in opposite directions.

* * * * *